United States Patent
Bremer et al.

(10) Patent No.: US 10,551,400 B2
(45) Date of Patent: *Feb. 4, 2020

(54) DEVICE FOR SOLID-PHASE MICROEXTRACTION

(71) Applicant: GERSTEL Systemtechnik GmbH & Co. KG, Mülheim (DE)

(72) Inventors: Ralf Bremer, Oberhausen (DE); Bernhard Rose, Düsseldorf (DE)

(73) Assignee: GERSTEL Systemtechnik GmbH & Co. KG, Mulheim (DE)

( * ) Notice: Subject to any disclaimer, the term of this patent is extended or adjusted under 35 U.S.C. 154(b) by 211 days.

This patent is subject to a terminal disclaimer.

(21) Appl. No.: 15/832,964

(22) Filed: Dec. 6, 2017

(65) Prior Publication Data

US 2018/0156836 A1 Jun. 7, 2018

Related U.S. Application Data

(63) Continuation of application No. 14/664,558, filed on Mar. 20, 2015, now Pat. No. 9,869,688.

(30) Foreign Application Priority Data

Mar. 31, 2014 (DE) .................. 10 2014 004 701

(51) Int. Cl.
*G01N 35/10* (2006.01)
*G01N 30/06* (2006.01)
(Continued)

(52) U.S. Cl.
CPC ......... *G01N 35/1079* (2013.01); *B01D 53/02* (2013.01); *G01N 1/405* (2013.01);
(Continued)

(58) Field of Classification Search
CPC ........... G01N 35/1081; G01N 35/1079; G01N 30/24; G01N 30/06; G01N 2030/062;
(Continued)

(56) References Cited

U.S. PATENT DOCUMENTS 9,869,688 B2  1/2018 Bremer et al.
2002/0066712 A1* 6/2002 Brockwell .......... B01L 3/50825
                                                        215/247
(Continued)

FOREIGN PATENT DOCUMENTS

DE    69102700 T2    1/1995
DE    10219790 C1   10/2003
(Continued)

OTHER PUBLICATIONS

European Search Report for EP 15000887 dated Aug. 27, 2015, 6 pages.

*Primary Examiner* — Nathaniel J Kolb
(74) *Attorney, Agent, or Firm* — Kilpatrick Townsend & Stockton LLP

(57) ABSTRACT

Device for solid-phase microextraction and analysis of substances to be analyzed, in particular in a gas chromatograph, with at least one collector, which is made of sorbent and/or adsorbent material and is placed on a rod-like support, and with at least one sample container, which is sealed with a pierceable partition wall and into which the collector is introduced piercing the partition wall for a sampling time, wherein the sealing of the sample container is assembled from the pierceable partition wall and a clamping ring, which can be mounted on the sample container and presses the partition wall together with a sealing element onto an upper rim of the sample container, and which comprises a socket in which a fitting of a transport adapter which is attached to a handling end of the rod-like support can be anchored detachably and with sealing surface pressure after the collector is inserted into the sample container following piercing the partition wall.

16 Claims, 9 Drawing Sheets

Figure 1:
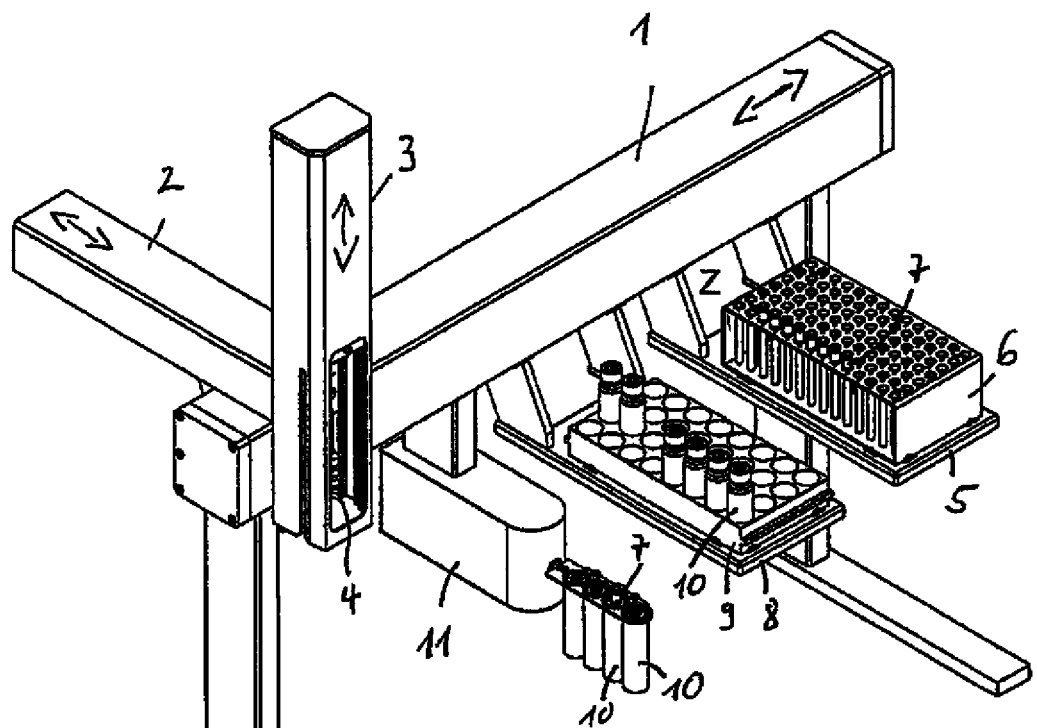

(51) Int. Cl.
    *G01N 30/24*     (2006.01)
    *B01D 53/02*     (2006.01)
    *G01N 1/40*     (2006.01)
    *G01N 30/00*     (2006.01)
    *G01N 35/00*     (2006.01)
    *B01L 3/00*     (2006.01)
    *B01L 9/06*     (2006.01)

(52) U.S. Cl.
    CPC .............. *G01N 30/06* (2013.01); *G01N 30/24* (2013.01); *G01N 35/1081* (2013.01); *B01D 2253/10* (2013.01); *B01D 2253/202* (2013.01); *B01L 3/5029* (2013.01); *B01L 9/06* (2013.01); *B01L 2200/0689* (2013.01); *B01L 2200/18* (2013.01); *B01L 2300/044* (2013.01); *B01L 2300/069* (2013.01); *B01L 2300/123* (2013.01); *G01N 35/0099* (2013.01); *G01N 2030/009* (2013.01); *G01N 2030/062* (2013.01); *G01N 2035/00524* (2013.01); *G01N 2035/1053* (2013.01)

(58) Field of Classification Search
    CPC ............... G01N 1/405; B01L 2300/044; B01L 2200/0689; B01D 53/02
    See application file for complete search history.

(56) References Cited

U.S. PATENT DOCUMENTS

| | | | |
|---|---|---|---|
| 2003/0200796 A1* | 10/2003 | Pawliszyn | G01N 30/00 73/64.47 |
| 2004/0037747 A1 | 2/2004 | Sternberger et al. | |
| 2005/0229723 A1* | 10/2005 | Bremer | G01N 30/24 73/864.81 |
| 2009/0199621 A1 | 8/2009 | Land, III | |
| 2012/0264227 A1* | 10/2012 | Couch | G01N 1/405 436/173 |

FOREIGN PATENT DOCUMENTS

| | | |
|---|---|---|
| EP | 1406077 B1 | 4/2004 |
| WO | 2007/032039 A2 | 3/2007 |

* cited by examiner

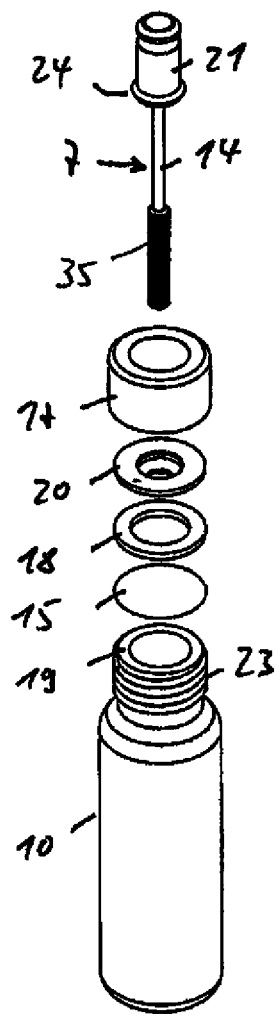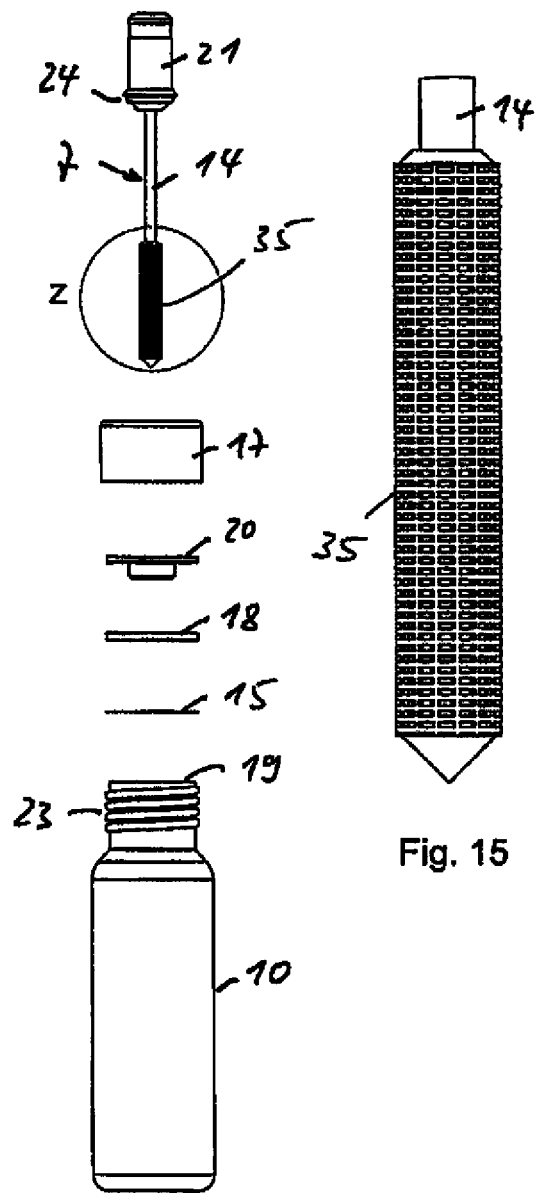
Fig. 13
Fig. 14
Fig. 15

DEVICE FOR SOLID-PHASE MICROEXTRACTION

CROSS-REFERENCE TO RELATED APPLICATIONS

This application is a continuation of U.S. patent application Ser. No. 14/664,558, filed Mar. 20, 2015, which claims priority to German Patent Application No. 102014004701.6, filed Mar. 31, 2014.

The invention relates to a device for solid-phase microextraction and analysis of substances to be analyzed, in particular for being inserted into a thermodesorption device of a gas chromatograph, according to the preamble of Claim 1.

Analytical instruments are used for the qualitative and quantitative determination of the constituents of samples, in particular using chromatographic separation methods. The efficiency of the separating techniques can generally be enhanced by suitable sample preparation or sample introduction. The user achieves a maximum level of precision, reproducibility and sample throughput only if he succeeds in automating the sampling procedure. For chromatographs, in particular gas chromatographs, automated sample preparation and sample injection devices are thus known, which are called autosamplers.

DE 102 19 790 C1 discloses such an autosampler, which comprises a receiving arm for a holder of a sampler, said receiving arm being movable in three directions perpendicular to one another. Autosamplers of this kind are designed for a predetermined, simple sequence, for example sampling by means of a syringe from an ampoule (vial) and introduction of the sample in a sample introduction system of an analytical instrument, and for a type of sampler proposed for this sequence, for example syringes of a specific size. It is therefore also known to provide several mountings for a receiving arm.

To perform solid-phase microextraction (SPME), it is known from DE 691 02 700 T2 to use a fibre which is contained in a housing and functions as adsorbent. The fibre is initially located in a needle which is used as a housing and which can pierce the septum of a sample container. The fibre, being attached to a syringe plunger, can then be guided out of the needle. After a defined sampling time in which the analytes diffuse to the solid phase and are adsorbed there, the needle is pulled back and then introduced into the injector of a gas chromatograph. This is followed by the thermodesorption of the analytes and their gas chromatographic separation and determination. The collection can take place both in a liquid matrix and also in the gas phase above liquids or solids, using what is called the headspace technique. The solid-phase microextraction by means of a fibre can be fully automated and is used, for example, for analysis of pesticides in water samples. A disadvantage is that the use of the fibres requires a complicated handling system with syringes.

EP 1 405 077 B1 discloses a collector for solid-phase microextraction and analysis of substances to be analyzed, which collector can be used both as a passive collector and also as a stirring element in a carrier liquid. For this purpose, the collector is composed of a rod-like support onto which a tube material is pushed as adsorbent. With the tube, a weighable phase and therefore a defined amount of active phase is attached to the support. Reproducible measurement results are thus achieved. A disadvantage is that this stand-alone collector, due to its lack of connection to a syringe, makes automated use difficult.

The object of the invention is therefore to provide a device for solid-phase microextraction that improves the handling of samples for analysis.

This object is achieved by the features of Claim 1.

Hereby, a device for solid-phase microextraction and analysis of substances to be analyzed, in particular for being inserted into a thermodesorption device of a gas chromatograph, is provided which mechanizes the detection of substances on the solid phase of the collector in an improved manner. Automation of the use of collectors is facilitated, specifically irrespective of whether the collector is designed as a fibre, as a tube material pushed onto a support, or as some other adsorbent.

According to the invention, the respective sample container is provided with a clamping ring as a cap, which clamping ring is an installation base for a transport adapter. The transport adapter provides, on the one hand, a terminal head which can be attached with seal seat and provides, on the other hand, a terminal inset for the collector. Being a terminal head, the transport adapter can be gripped by an automated gripper or a movable receiving arm and ensures at the same time that the sample container is sealed by the transport adapter when the collector is inserted. Besides a self-sealing septum, it is then possible to use in particular partition walls or separating walls that can be easily pierced mechanically. These are, for example, membranes, metal or plastic sheets, or elastically deformable passage-closing elements.

The installation base designed as a clamping ring permits in a simple way the insertion of a sealing element, the deformation of which generates the sealing function at the neck of the sample container when the clamping ring is mounted.

The use of O-rings as sealing elements is preferred, since these permit a sealing function by axial and also radial deformation. The attachment of the transport adapter to the clamping ring can thus easily take place through radial deformation of the sealing element, as a result of which in addition a holding force between clamping ring and transport adapter can be generated, which force exceeds the inherent weight force of the sample container containing a sample. Consequently, the sample container can be transported by the transport adapter and optionally be treated, for example in shaking devices, etc.

The collector is placed on the rod-like support and can be a fibre or can line the rod-like support with a wide variety of materials that function as adsorbent. Since the partition wall can be designed to be easy to pierce mechanically, supports lined with a collector can be used as piercing members having diameters in the range of several millimetres, for example 1 to 5 mm. By contrast, the diameter of the fibres used in the prior art varies between 0.05 and 1 mm. In particular, supports lined with a tube-like adsorbent can now also, as inserts guided by a holder, be introduced in an automated manner into sample containers and removed therefrom.

Further embodiments and advantages of the invention are set forth in the following description and in the dependent claims.

The invention is explained in more detail below on the basis of the embodiments shown in the attached figures.

Figure 2:
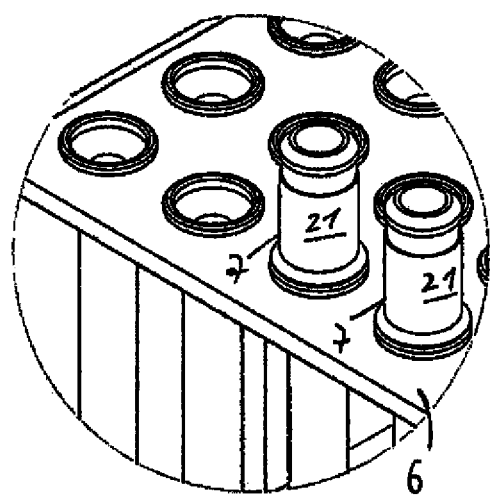
Figures 3, 4:
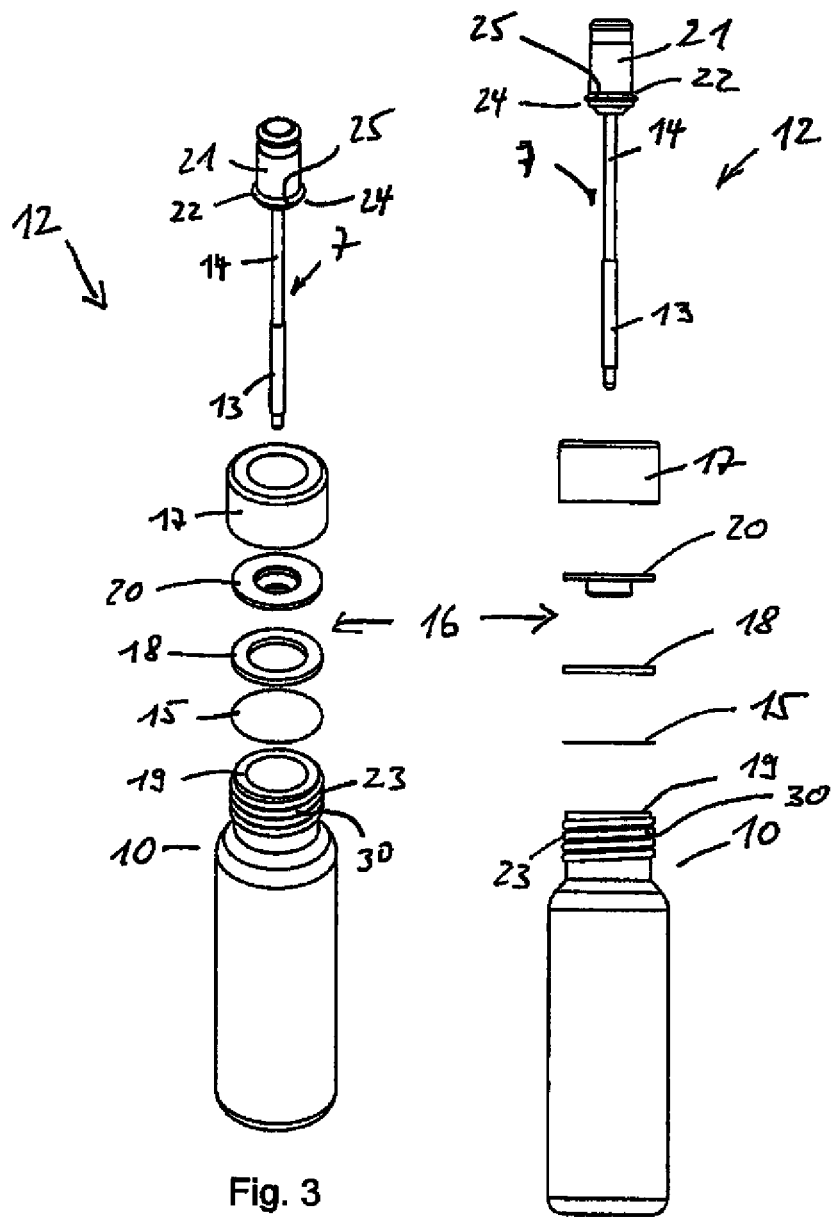
Figures 5, 6:
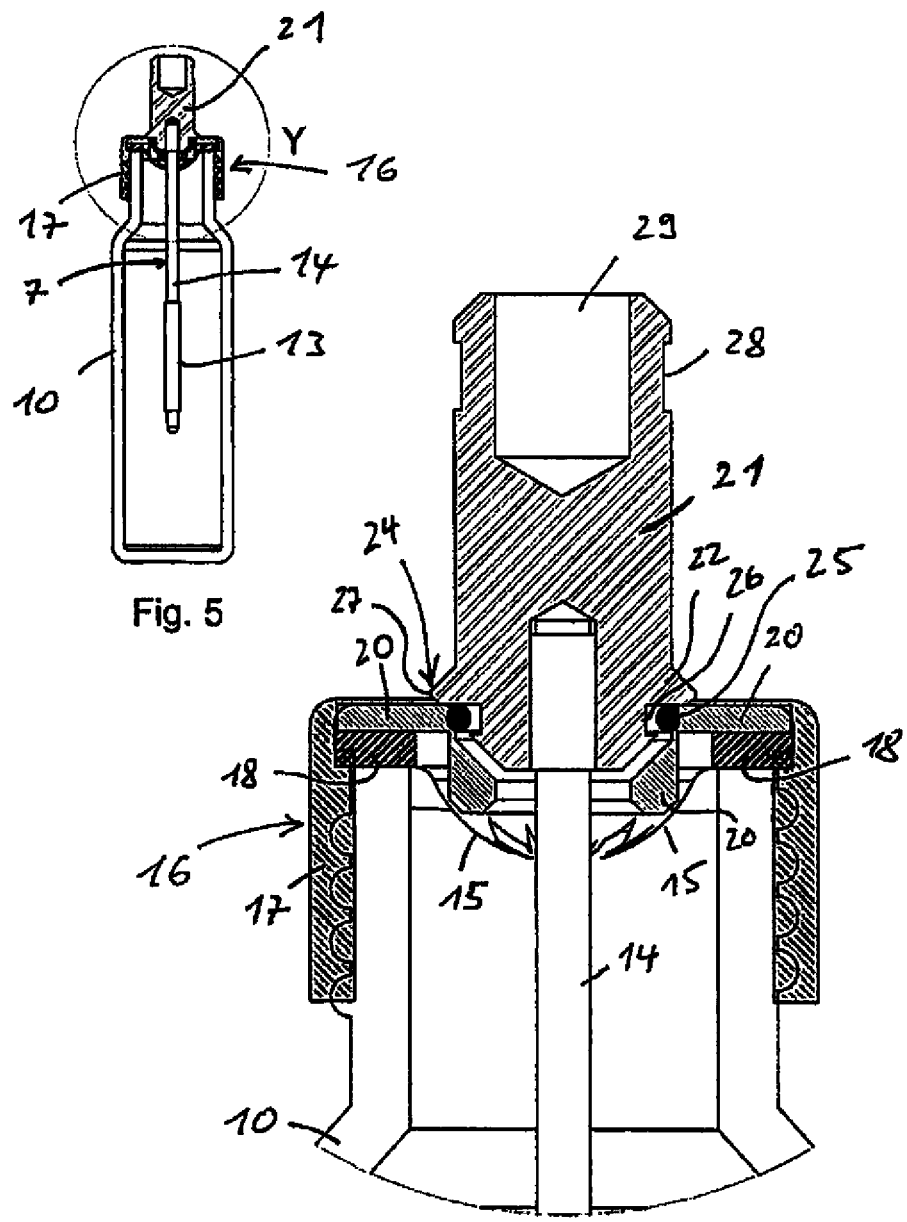
Figure 7:
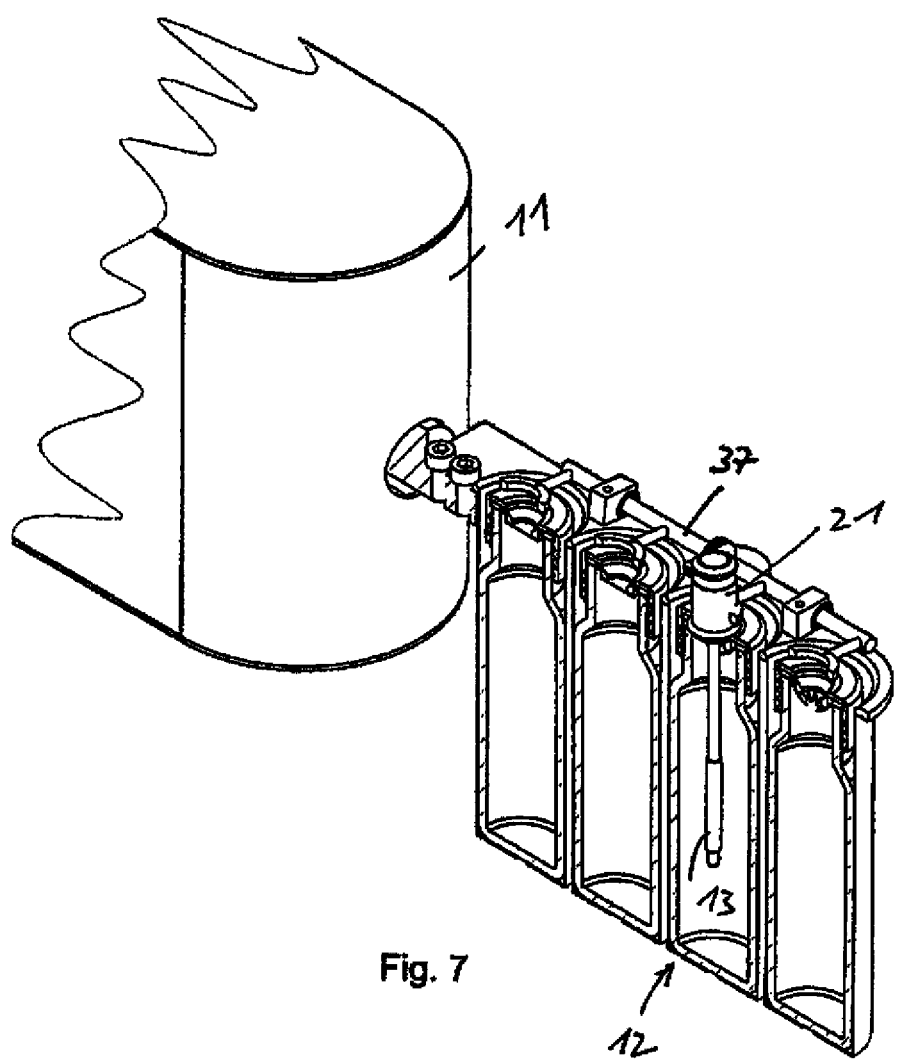
Figure 8:
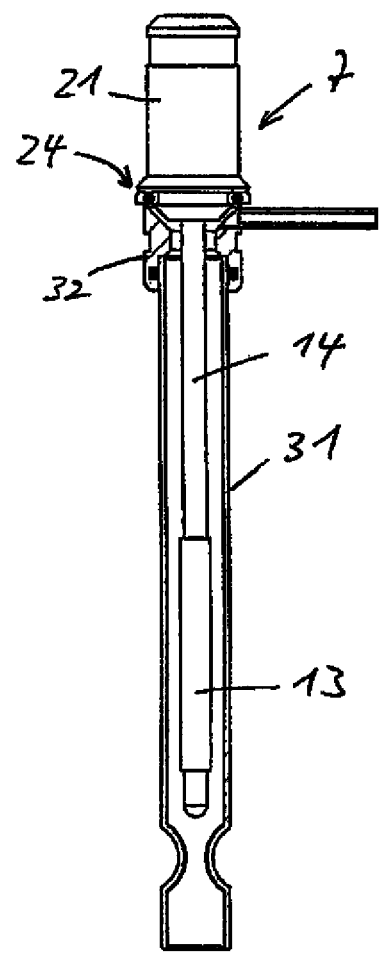
Figures 9, 10:
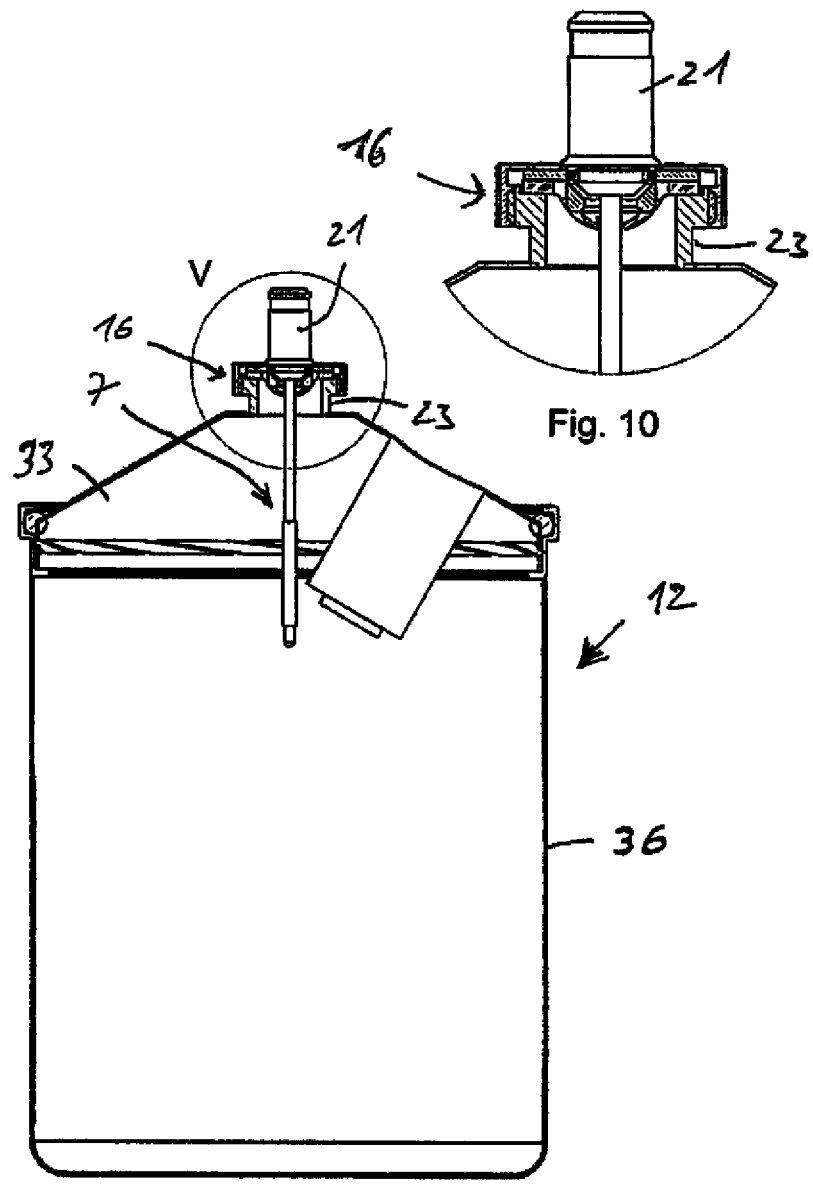
Figure 11:
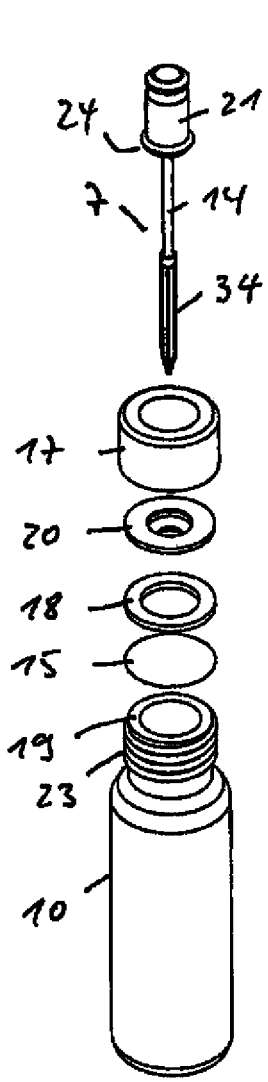
Figure 12:
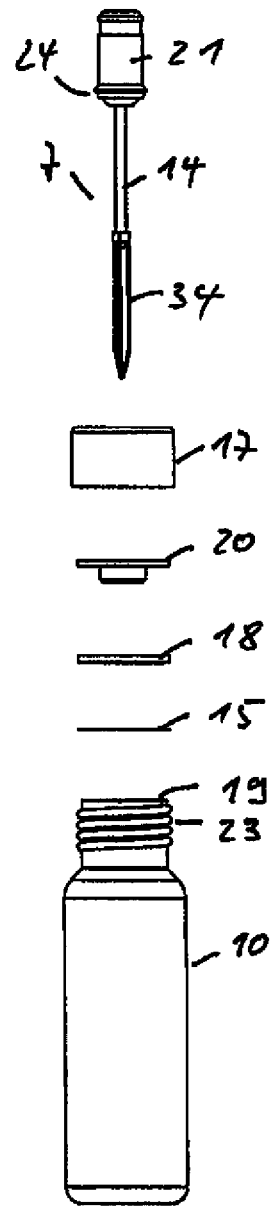
Figures 16, 17:
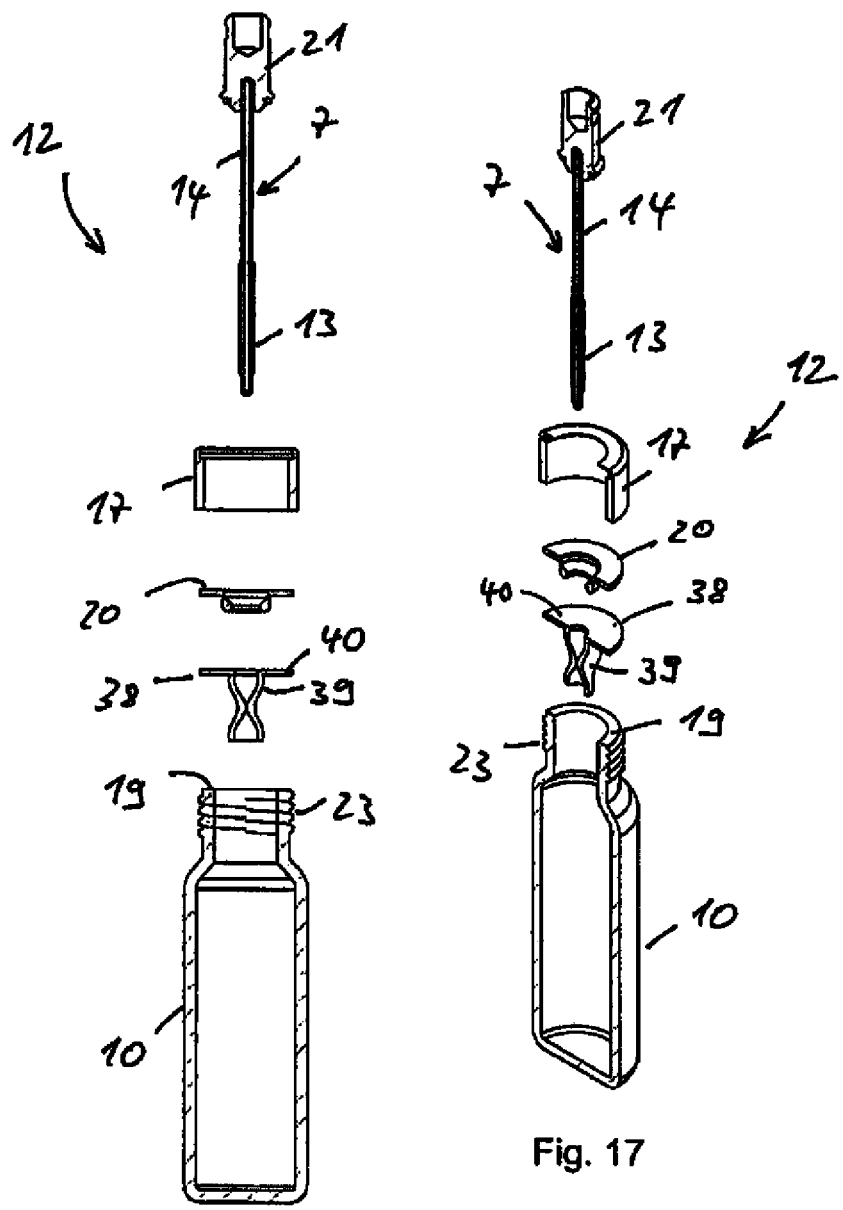

FIG. 1 shows schematically a perspective view of a device for sample handling with devices for solid-phase microextraction according to a first embodiment, FIG. 2 shows the detail Z from FIG. 1 in an enlarged view, FIG. 3 shows, schematically and in perspective, an exploded view of the device for solid-phase microextraction according to the first embodiment, FIG. 4 shows schematically a side view of the exploded view according to FIG. 3, FIG. 5 shows schematically a longitudinal section through the device for solid-phase microextraction according to the first embodiment, FIG. 6 shows the detail Y from FIG. 5 in an enlarged view, FIG. 7 shows schematically and in a partially sectioned view, a vibrator into which a device for solid-phase microextraction according to the first embodiment is inserted, FIG. 8 shows schematically a longitudinal section through the device for solid-phase microextraction according to a second embodiment, FIG. 9 shows schematically and in a partially sectioned view, a device for solid-phase microextraction according to a third embodiment, FIG. 10 shows the detail V from FIG. 9 in an enlarged view, FIG. 11 shows, schematically and in perspective, an exploded view of the device for solid-phase microextraction according to a fourth embodiment, FIG. 12 shows schematically a side view of the exploded view according to FIG. 11, FIG. 13 shows, schematically and in perspective, an exploded view of the device for solid-phase microextraction according to a fifth embodiment, FIG. 14 shows schematically a side view of the exploded view according to FIG. 13, FIG. 15 shows the detail Z from FIG. 14 in an enlarged view, FIG. 16 shows schematically a side view of an exploded view of the device for solid-phase microextraction according to a sixth embodiment, and FIG. 17 shows, schematically and in perspective, and partially sectioned, the exploded view according to FIG. 16.

The invention relates to a device for solid-phase microextraction and analysis of substances to be analyzed, in particular for being inserted into a thermodesorption device of a gas chromatograph. To automate the solid-phase microextraction, the sampling of samples for sample preparation or sample introduction is preferably carried out by means of so-called autosamplers or XYZ robots.

FIG. 1 and FIG. 2 show an autosampler for sampling. The autosampler preferably comprises a horizontal carriage guide 1 for a cross slide 2, which is movable along the carriage guide 1 and is also preferably movable in the plane of the carriage guide 1 perpendicular to the carriage guide 1, such that all stations can be served. A receiving arm 3, which is preferably vertically movable, is located at the end of the cross slide 2.

The movable receiving arm 3 is designed to alternately hold at least one sampler 4. The receiving arm 3 serves to move the respective sampler 4 to desired positions. According to FIG. 1, the autosampler comprises a first tray holder 5 for a collector tray 6, in which a number of collecting means 7 for use in a sampling procedure are placed. The autosampler further comprises a second tray holder 8 for a sample container tray 9, in which a number of sample containers 10 containing samples are placed. The receiving arm 3 allows to travel to selectable positions above of the collector tray 6 and the sample container tray 9, for example in order to grip a collecting means 7, transport it and insert it into a sample container 10 for a selectable sampling time.

According to FIG. 1, the autosampler also preferably comprises a vibrator or shaker 11, which moves some or all of the sample containers 10 provided with a collecting means 7, in order to accelerate the transport of substances to the solid phase. The collection can take place both in a liquid matrix and also in the gas phase above liquids or solids, using what is called the headspace technique.

Samples are taken from the sample containers 10 using the collecting means 7, as the collecting means 7 are being inserted into the respective sample containers 10, which contain samples, for a selectable sampling time by moving up and down the sampler 4. The movement is performed by the movable receiving arm 3. The preferred direction of movement is a vertical movement of the sampler 4 for sampling.

As FIG. 3 and FIG. 4 show, for solid-phase microextraction and analysis of substances to be analyzed, in particular for being inserted into a thermodesorption device of a gas chromatograph, a device 12 with a collecting means 7 and a sample container 10 is provided, which, according to a first embodiment, are configured as follows. The device 12 comprises at least one collector 13, which is made of sorbent and/or adsorbent material and is placed on a rod-like support 14. The device 12 further comprises at least one sample container 10, which is sealed with a pierceable partition wall 15 or separating wall. Piercing the partition wall 15, the collector 13 can be introduced into the sample container 10 for a sampling time. The sealing by means of the partition wall 15 is designed in particular to be leaktight to fluids.

A sealing 16 of the sample container 10 is assembled from the pierceable partition wall 15 and a clamping ring 17, which can be mounted on the sample container 10. The clamping ring 17 presses the partition wall 15 together with a sealing element 18 onto an upper rim 19 of the sample container 10. The sealing 16 moreover comprises a socket 20 which is used in the press fit between clamping ring 17 and upper rim 19 of the sample container 10 or, for example, can be designed in one piece (not shown) with the clamping ring 17. The socket shapes an adapter mating piece for a transport adapter 21 (cf. FIG. 6), which is attached to a handling end of the rod-like support 14. The sealing element 18 can be designed as an O-ring.

The transport adapter 21 has a fitting 22 which can be anchored in the socket 20 with sealing surface pressure 24, for detachably anchoring the transport adapter 21 on the sealing 16 of the sample container 10 after the collector 13 is inserted into the sample container 10 following piercing the partition wall 15, as is shown in particular in FIG. 5 and FIG. 6.

The clamping ring 17 is here screwed as a securing ring onto the neck 23 of the sample container 10 by means of a screw closure 30. Alternatively, the clamping ring 17 can also be squeezed on or latched on.

The pierceable partition wall 15 is preferably designed as a membrane or a metal or plastic sheet. Examples of materials for the sheets are aluminium, Teflon and polypropylene. The material for the sheets is preferably chemically inert to the samples that are to be introduced or that have been introduced. The sheet, which is mechanically easily pierceable, in particular also by the collector 13 with diameters of greater than 1 mm, replaces the septum as sealing for the sample container 10. In the device 12, the sealing effected by the septum is provided by the partition wall 15 in conjunction with the sealing surface pressure 24 and the sealing element 18, which seal the transport adapter 21 in relation to the clamping ring 17 and seal the clamping ring 17 in relation to the sample container 10. The sealing is preferably gas-tight.

Thus, according to the invention, a sealing system with preferably two sealing rings is provided in order to prohibit a material flow between the functionally separate spaces of a sample container 10 and of an external environment after the partition wall 15 has been pierced and while the collector 13 is inserted, specifically with simultaneous provision of a collecting means 7 which, for sampling and sample delivery, can be gripped and transported by an automated sampler or robot. It is thereby ensured that, irrespective of the material of the partition wall 15, the sample container 10 is still sealed even after the partition wall 15 has been pierced. This applies in particular to materials that have no inherent elastic closing effect, as for example metal sheets, in which the piercing can, for example, cause a puncturing.

As FIG. 5 and FIG. 6 show in particular, the transport adapter 21 has, for the sealing surface pressure 24, preferably an annular groove 26 for inserting a seal by means of O-ring 25 that can be pressed in radially into the socket 20. The sealing surface pressure 24 can be configured in such a way that its holding force is sufficient to move the sample container 10 via the transport adapter 21, without additional holding means being needed. On the fitting 22, there can be a protruding edge 27 (cf. FIG. 6) which acts as a limit stop on the socket 20. The sealing surface pressure 24 between the fitting 22 of the transport adapter 21 and the socket 20 of the sealing 16 can then be reliably positioned.

The transport adapter 21 can have connecting elements 28, 29 for different installation situations on a sampler 4.

The collector 13 comprises, for example, a tube of sorbent and/or adsorbent material which is pushed onto the rod-like support 14. Alternatively, in order to provide the collector 13, the support 14 can be lined with a wide variety of materials as adsorbent. The support 14 preferably has a diameter in the range of 1 to 6 mm. The lining with the adsorbent can, for example, lie in a thickness range of 0.05 to 2 mm. The support 14 can alternatively be designed as a tube (not shown), for example in order to be able to perform additional dosing via the collecting means 7 during a sampling procedure in the sample container 10.

The device 12 can be moved as a transportable sampler to various treatment stations, for example a vibrator/shaker 11, as shown in FIG. 7. In order to secure the device 12 in the process, a holding means 37 can be provided. In addition, a temperature control of the device 12 can be provided.

As FIG. 8 shows, the collecting means 7 can be inserted into a flow through tube 31 for the sampling or after completion of the sampling, in which case the sealing surface pressure 24 of the transport adapter 21 can take place with an attachment head 32 at the insertion end of the tube 31.

As FIG. 9 and FIG. 10 show according to a third embodiment, the collector 13 for adsorption or desorption of the collected substances can be introduced into a pressurized container 36 as headspace container. The pressurized container 36 has a lid 33 which, at the head end, has a neck 23 for attachment of the sealing 16, as described above. The transport adapter 21 can also be used for desorption purposes if the associated devices are assigned a sealing 16 as described above.

FIG. 11 and FIG. 12 show a fourth embodiment of the device 12, which differs from the first embodiment according to FIG. 3 and FIG. 4 in that the collector 13 comprises a fibre and a cage 34 surrounding the fibre. Otherwise, the details given above regarding the first embodiment apply accordingly.

FIG. 13 to FIG. 15 show a fifth embodiment of the device 12, in which the collector 13 comprises a flow through hollow body 35, which has a preferably lattice-like outer wall and into which powdery sorbent and/or adsorbent material is inserted. Otherwise, the details given above regarding the first embodiment apply accordingly.

FIG. 16 and FIG. 17 show a sixth embodiment of the device 12, in which the sealing 16 has a pierceable functional partition wall 38. This functional partition wall 38 is provided by an elastically deformable passage-closing element 39, which is here designed as an elastic conical seal, for example. When this elastic passage-closing element 39 is penetrated, the collecting means 7, upon insertion into the sample container 10, presses the wall of the passage-closing element 39 slightly to the side. A sealing disc 40 can be placed directly on the functional partition wall 38 and can be pressed with the clamping ring 17 sealingly onto the upper rim 19 of the sample container 10. In addition to or as an alternative (not shown) to the sealing disc 40, the sealing element 18 can be provided as described above. Otherwise, the details given above regarding the first embodiment apply accordingly.

As the sorbent and/or adsorbent material for the collector 13, a material can be chosen, for example, from the group comprising polyethylene glycol, silicone, octadecyltrichlorosilane, polymethylvinyl chlorosilane, liquid-crystalline polyacrylates, grafted self-organized monomolecular layers, graphene, carbon nanotubes, ionic liquids and inorganic coating materials.

After a sampling procedure, the collecting means 7 with the collector 13 can be introduced in a known manner into a thermodesorption device. Instead of being desorbed in a thermodesorption device, the collecting means 7 can also be introduced into an extraction device containing an organic liquid, said organic liquid being one that has a high level of interaction with the substances that are to be analyzed.

The substances desorbed from the collecting means 7 are preferably fed to an introduction device, for example of a gas chromatograph, in order to be brought to analysis by means of a carrier gas for example via a separating column of a gas chromatograph.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The invention claimed is:

1. A device for solid-phase microextraction and analysis of substances to be analyzed with at least one collector, wherein the collector comprises a rod-like support having a diameter in the range of 1 mm to 6 mm, and a tube of sorbent or adsorbent material which is pushed onto the rod-like support, the tube having a wall thickness in the range of 0.05 mm to 2 mm; wherein the device further comprises at least one sample container, which is sealed with a pierceable partition wall and into which the collector is introduced by piercing the partition wall for a sampling time, the sealing by means of the partition wall is designed to be leak-tight to fluids, wherein the seal of the sample container is assembled from the pierceable partition wall and a clamping ring, which can be mounted on the sample container and presses the partition wall together with an insertable sealing element onto an upper rim of the sample container, and wherein the seal comprises a socket secured between the clamping ring and the upper rim of the sample container, wherein a fitting of a transport adapter can be detachably anchored within the socket with sealing surface pressure after the support lined with the collector is inserted into the sample container following piercing the partition wall.

2. The device according to claim 1, wherein the pierceable partition wall is designed as a membrane, a metal or plastic sheet or an elastically deformable passage-closing element.

3. The device according to claim 1, wherein the transport adapter has an annular groove for inserting an O-ring seal, wherein the O-ring-seal can be pressed in radially into the socket.

4. The device according to claim 1, wherein an adapter mating piece of the socket can be inserted into the clamping ring, wherein the adapter mating piece is shaped to receive the transport adapter.

5. The device according to claim 1, wherein the transport adapter comprises a number of different interchangeable connecting elements, each of the connecting elements being configured for use with a different type of installation connection.

6. The device according to claim 1, wherein the collector comprises a fibre and a cage surrounding the fibre.

7. The device according to claim 1, wherein the collector is a tube made of sorbent material which is pushed onto the rod-like support.

8. The device according to claim 1, wherein the collector comprises a flow through hollow body, with a powdery sorbent or adsorbent material inserted therein.

9. The device according to claim 1, wherein, in order to automate the solid-phase microextraction, the transport adapter provides a terminal head that is graspable by movable receiving arms of autosamplers.

10. The device according to claim 1, wherein the clamping ring can be mounted onto the neck of the sample container via a screw closure.

11. The device according to claim 1, wherein the sorbent or adsorbent material is a material from the group comprising polyethylene glycol, silicone, octadecyltrichlorosilane, polymethylvinyl chlorosilane, liquid-crystalline polyacrylates, grafted self-organized monomolecular layers, graphene, carbon nanotubes, ionic liquids and inorganic coating materials.

12. The device according to claim 1, wherein the substances to be analyzed are analyzed in a gas chromatograph.

13. The device according to claim 1, wherein the partition wall in conjunction with the sealing surface and the sealing element seal the transport adapter in relation to the clamping ring in relation to the sample container.

14. The device according to claim 1, wherein the transport adapter is attached to a handling end of the rod-like support.

15. A device for solid-phase microextraction and analysis of substances to be analyzed, the device comprising:

at least one collector, wherein the collector comprises a rod-like support, and a tube of sorbent or adsorbent material which is pushed onto the rod-like support;

at least one sample container having a pierceable partition wall and into which the collector is configured to be introduced by piercing the partition wall for a sampling time, wherein the partition wall forms a seal that is configured to be leak-tight to fluids, wherein the seal of the sample container is assembled from the pierceable partition wall and a clamping ring, which is mountable on the sample container and presses the partition wall together with an insertable sealing element onto an upper rim of the sample container, and wherein the seal comprises a socket secured between the clamping ring and the upper rim of the sample container; and a transport adapter operably attached to the collector, the transport adapter having a fitting that is configured to be detachably anchored within the socket with sealing surface pressure after the support lined with the collector is inserted into the sample container following piercing the partition wall.

16. A device as in claim 15, wherein the rod-like support has a diameter in the range of 1 mm to 6 mm, and the tube has a wall thickness in the range of 0.05 mm to 2 mm.

* * * * *